(12) United States Patent
Huo et al.

(10) Patent No.: US 7,476,739 B2
(45) Date of Patent: Jan. 13, 2009

(54) ISOMERIZATION OF TRIS-CYCLOMETALLATED IRIDIUM COMPLEXES

(75) Inventors: Shouquan Huo, Webster, NY (US); Joseph C. Deaton, Rochester, NY (US); Denis Y. Kondakov, Kendall, NY (US)

(73) Assignee: Eastman Kodak Company, Rochester, NY (US)

( * ) Notice: Subject to any disclaimer, the term of this patent is extended or adjusted under 35 U.S.C. 154(b) by 615 days.

(21) Appl. No.: 11/134,120

(22) Filed: May 20, 2005

(65) Prior Publication Data
US 2006/0264632 A1    Nov. 23, 2006

(51) Int. Cl.
*C07F 15/00* (2006.01)
(52) U.S. Cl. .......................................................... 546/4
(58) Field of Classification Search ........................ None
See application file for complete search history.

(56) References Cited

FOREIGN PATENT DOCUMENTS

JP        2004-189673        7/2004

OTHER PUBLICATIONS

S. Huo, "Facial Tris-Cyclometallated Group 9 Complex Synthesis", U.S. Appl. No. 11/015,910 (D-88413) filed Dec. 17, 2004, Reference C1.
A. B. Tamayo, et al., "Synthesis and Characterization of Facial and Meridional Tris-cyclometalated Iridium (III) Complexes", J. Am. Chem. Soc., 2003, pp. 7377-7387, Reference C2.

*Primary Examiner*—Zinna N Davis
(74) *Attorney, Agent, or Firm*—Arthur E. Kluegel; Raymond L. Owens

(57) ABSTRACT

A process for forming a facial tris-cyclometallated iridium or rhodium complex isomer comprises heating an original solid composition containing meridional isomer of the metal complex at a temperature and for a time sufficient to form a product containing the facial isomer in an increased ratio to meridional isomer compared to the original composition.

24 Claims, No Drawings

ISOMERIZATION OF TRIS-CYCLOMETALLATED IRIDIUM COMPLEXES

BACKGROUND OF THE INVENTION

Cyclometallated iridium complexes have been the focus of research and development in OLED (Mark E. Thompson et al, WO 01/41512 A1) display devices over last several years. Those complexes can offer higher efficiency when used as phosphorescent dopants in OLED devices since both singlet and triplet excitons generated by electroexcitation can be harvested by a phosphorescent dopant, while only singlets (25% of total excitons) can be utilized when a fluorescent material is used as a dopant. Tris-cyclometallated iridium complexes have demonstrated such advantage. There exist two stereoisomers in homoleptic tris-cyclometallated iridium complexes such as tris(2-(phenyl)pyridinato-N,$C^2$)iridium (III) (Ir(ppy)$_3$), namely facial and meridional isomers as shown below. The facial isomer has been shown to be more desirable as it has demonstrated higher quantum yield and thermal stability than the corresponding meridional isomer (A. B. Tamayo, et al, *J. Am. Chem. Soc.* 2003, 125, 7377).

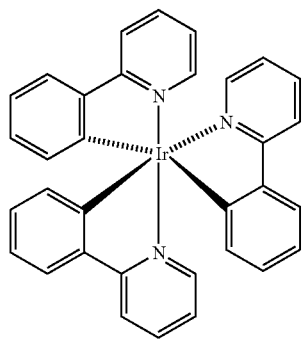

meridional Ir(ppy)$_3$

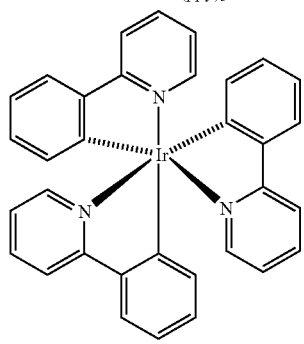

facial Ir(ppy)$_3$

There are continuous efforts to develop new phosphorescent dopants for improving the efficiency and operational stability of OLED devices. Heteroleptic (mixed) tris-cyclometallated iridium complexes have recently attracted attention of research community and their applications to OLED devices have been demonstrated (T. Igarashi et al, US 2001/0019782 A1; J. Kamatani, et al, US 2003/0068526 A1; S. Akiyama et al, JP2003-192691A). However, the synthesis of those heteroleptic complexes is challenging. The method employed in the prior arts involves the reaction of a bis-cyclometallated iridium complex with a third ligand in glycerol at high temperature (usually above 180° C.), which we found to produce a mixture of different homoleptic and heteroleptic tris-cyclometallated iridium complexes formed from ligand-scrambling side reactions and lead to difficulties in separation and purification of desired compounds. Recently, we have developed a novel method to prepare mixed tris-cyclometallated iridium complexes in high yields and purity, but the products obtained from this reaction are meridional isomers (S. Huo, U.S. Pat. No. 6,835,835). We also discovered that some meridional isomers could isomerize to their facial isomers by applying heat to a solution of the meridional isomer in DMSO, but it was accompanied by severe decomposition in some cases. Another method for this isomerization involves the use of an acid and silica gel particles US2006/0135772. Although the method allowed isolation of pure facial isomer readily, the yield of the product was not satisfactory. Thompson et al reported thermal (by refluxing the meridional isomer in glycerol) or photochemical isomerization of homoleptic meridional tris-cyclometallated iridium complexes (Tamayo et al, *J. Am. Chem. Soc.* 2003, 125, 7377-7387). A photochemical isomerization of homoleptic tris-cyclometallated iridium complexes from meridional isomers to facial isomers is also disclosed in a patent application (JP 2004189673 A2). However, we found that the methods did not work for some heteroleptic tris-cyclometallated iridium complexes such as meridional bis-(1-(phenyl) isoquinolinato-N, $C^2$)(phenylpyridinato-N,$C^2$)iridium (mer-Ir(1-piq)$_2$(ppy)). For example, thermal isomerization of mer-Ir(1-piq)$_2$(ppy) in glycerol under the same conditions described in literature (Tamayo et al, *J. Am. Chem. Soc.,* 2003, 125, 7377-7387) resulted in largely decompositions and severe ligand-scrambling. Photo irradiation of mer-Ir(1-piq)$_2$(ppy) did not produce the corresponding facial isomer. Moreover, the photochemical process may not be suitable for large scale productions and the use of glycerol is not convenient for isolation and purification of the product.

It is a problem to be solved to provide a simple and efficient process for the isomerization of meridional tris-cyclometallated iridium complexes to their facial isomers.

SUMMARY OF THE INVENTION

The invention provides a process for forming a facial tris-cyclometallated iridium or rhodium complex isomer comprising heating an original solid composition containing meridional isomer of the metal complex at a temperature and for a time sufficient to form a product containing the facial isomer in an increased ratio to meridional isomer compared to the original composition.

The process provides a simple and efficient process for the isomerization of meridional tris-cyclometallated iridium complexes to their facial isomers.

DETAILED DESCRIPTION OF THE INVENTION

The invention is summarized above. Tris-cyclometallated complexes related to the invention can be either homoleptic or heteroleptic complexes and may be represented by one of the following formulas:

$$ML_3 \qquad (1)$$

$$M(L')_2L'' \qquad (2)$$

$$ML'L''L''' \qquad (3)$$

wherein M is the metal Ir or Rh, L, L', L'', and L''' are monoanionic bidentate ligands that can be coordinated to M through a carbon and a heteroatom donor. Suitably, L, L', L", and L'" represent the ligand that can be coordinated to M through a carbon and a nitrogen donors. Conveniently, the ligand can be derived from phenylpyridine, phenylisoquinoline, phenylquinoline, phenylpyrimidine, and their derivatives and analogues.

The invention particularly relates to a process for forming a facial tris-cyclometallated iridium or rhodium complex isomer of formula $M(piq)_2(ppy)$ from the meridional isomer comprising subjecting a solid composition containing the meridional isomer to a thermal isomerization reaction, wherein piq is a 1- or 3-phenylisoquinoline group, and ppy is a 2-phenylpyridine group as represented by Equation 1:

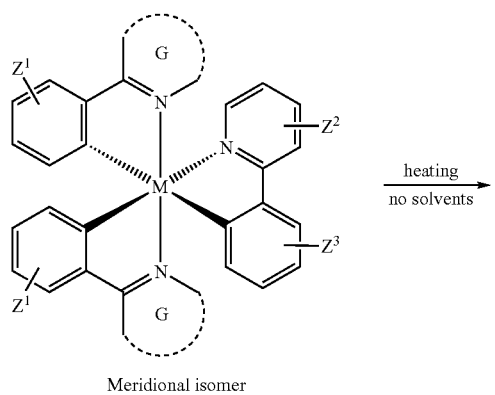

Meridional isomer heating
no solvents

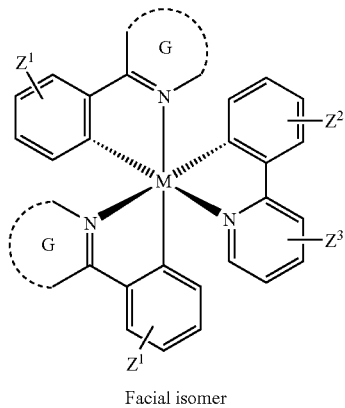

Facial isomer wherein,

M represents Ir or Rh, preferably Ir,

G represents an isoquinoline group, and $Z^1$, $Z^2$, and $Z^3$ represent hydrogen or one or more independently selected groups.

The facial isomer is defined as the stereoisomer of a tris-cyclometallated iridium complex wherein three monoanionic bidentate ligands coordinate to the metal with a facial arrangement of the three heteroatom donors and a facial arrangement of the three carbon donors. Similarly, the meridional isomer has a meridional arrangement of the three heteroatom donors and a meridional arrangement of the three carbon donors. As mentioned before, there exist two stereoisomers in homoleptic tris-cyclometallated iridium complexes where three ligands are the same, namely a facial and a meridional isomer. However, when three ligands that coordinate to the iridium are different from each other or two are the same and the third one is different, a heteroleptic tris-cyclometallated iridium complex is formed and the total number of meridional and facial isomers of this compound may be more than two. Examples of mer- and fac-isomers of heteroleptic tris-cyclometallated iridium complex $Ir(1-piq)_2(ppy)$ are shown below:

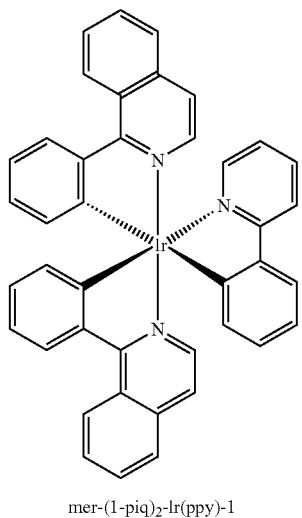

mer-(1-piq)$_2$-Ir(ppy)-1

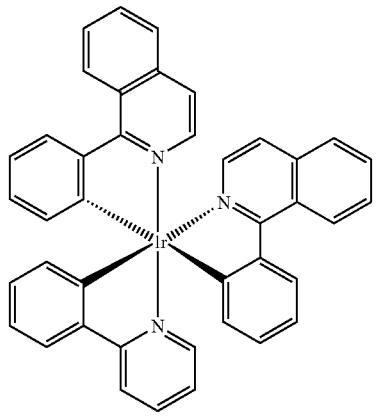

mer-(1-piq)$_2$-Ir(ppy)-2

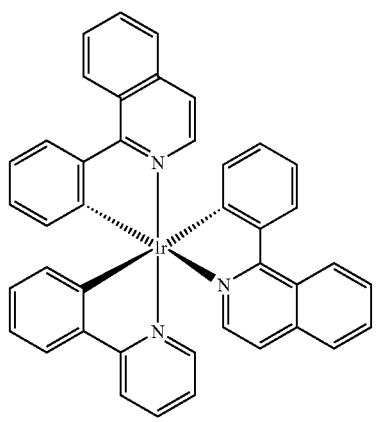

mer-(1-piq)$_2$-Ir(ppy)-3

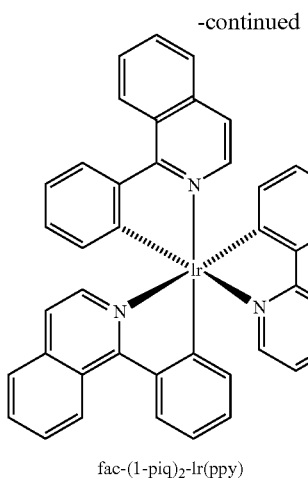

fac-(1-piq)₂-Ir(ppy)

The piq ligand can be a 1-phenylisoquinoline or a 3-phenylisoquinoline group as represented by the following formulas,

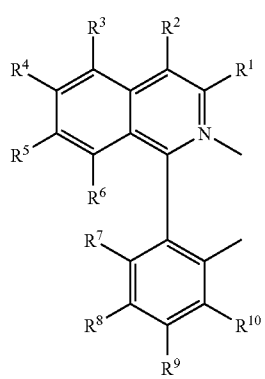

Wherein $R^1$-$R^{20}$ represent hydrogen or independently selected substituents. Suitably, the piq ligand is 1-phenylisoquinoline or 3-phenylisoquinoline group.

The ppy can be a 2-phenylpyridine group as represented by the following formula,

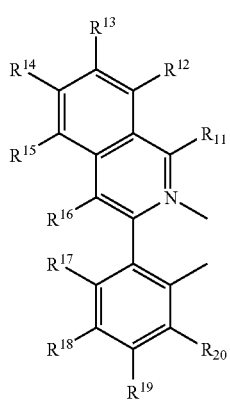

Wherein $R^{21}$-$R^{28}$ represent hydrogen or independently selected substituents, provided $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, as well as $R^{27}$ and $R^{28}$ can form a ring group. Conveniently, the ppy group can be chosen from the following:

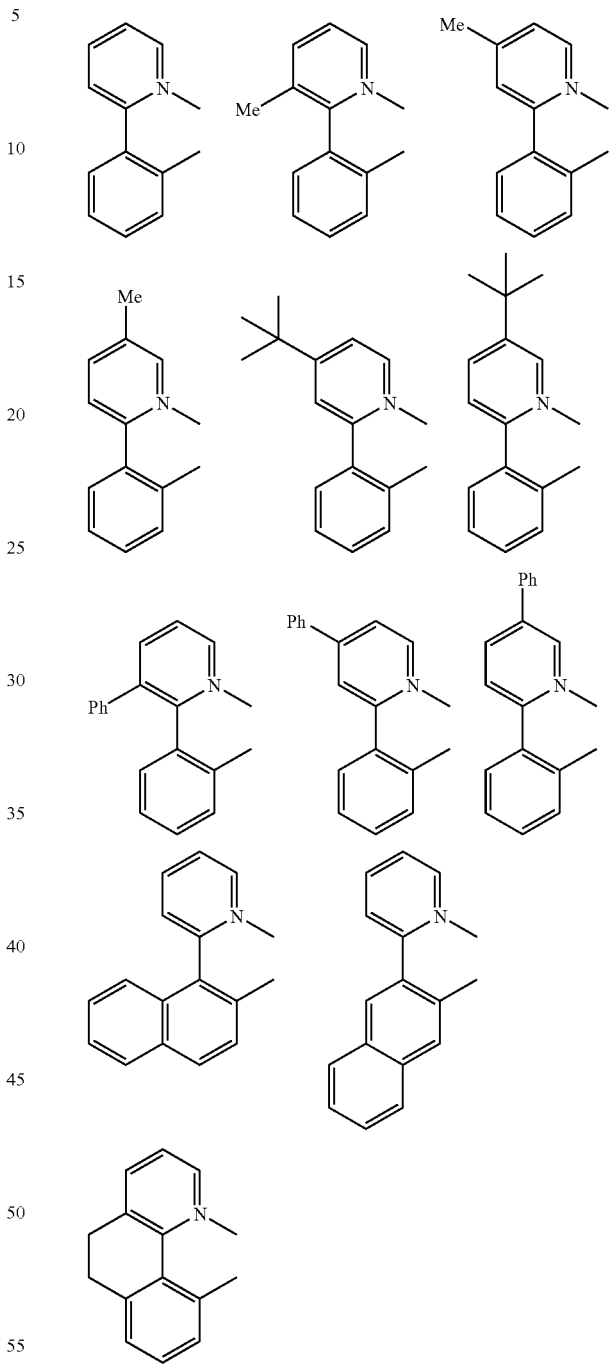

The precursors for the isomerization process, namely meridional tris-cyclometallated iridium complexes, can be prepared according to the procedure described in the prior art by reacting an organozinc complex of a desired organic ligand with a suitable halide-bridged di-nuclear bis-cyclometallated iridium complex (S. Huo, U.S. Pat. No. 6,835,835). They may also be prepared by other published methods (A. B. Tamayo, et al, *J. Am. Chem. Soc.* 2003, 125, 7377). Some representative meridional complexes are shown below,

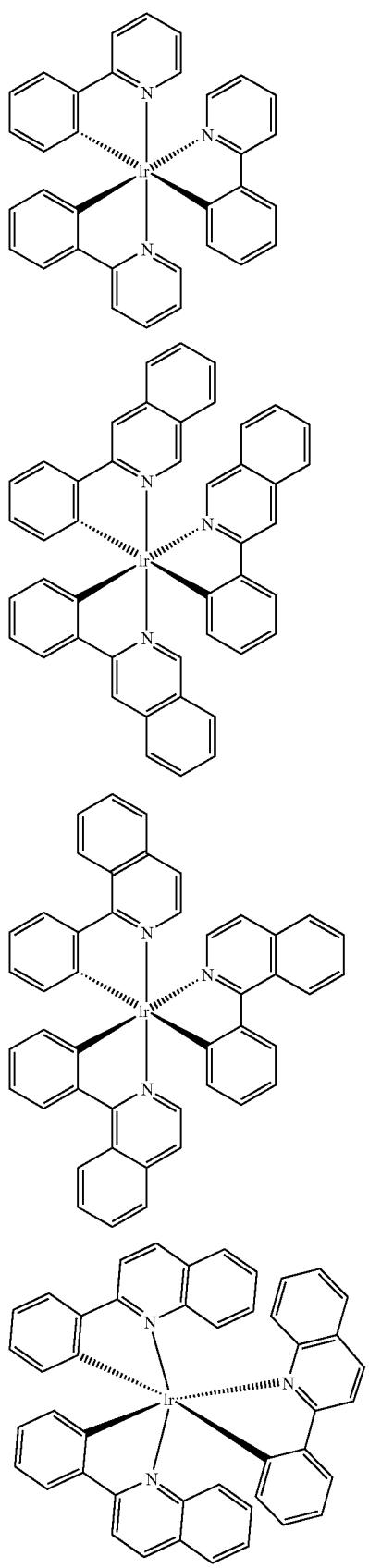
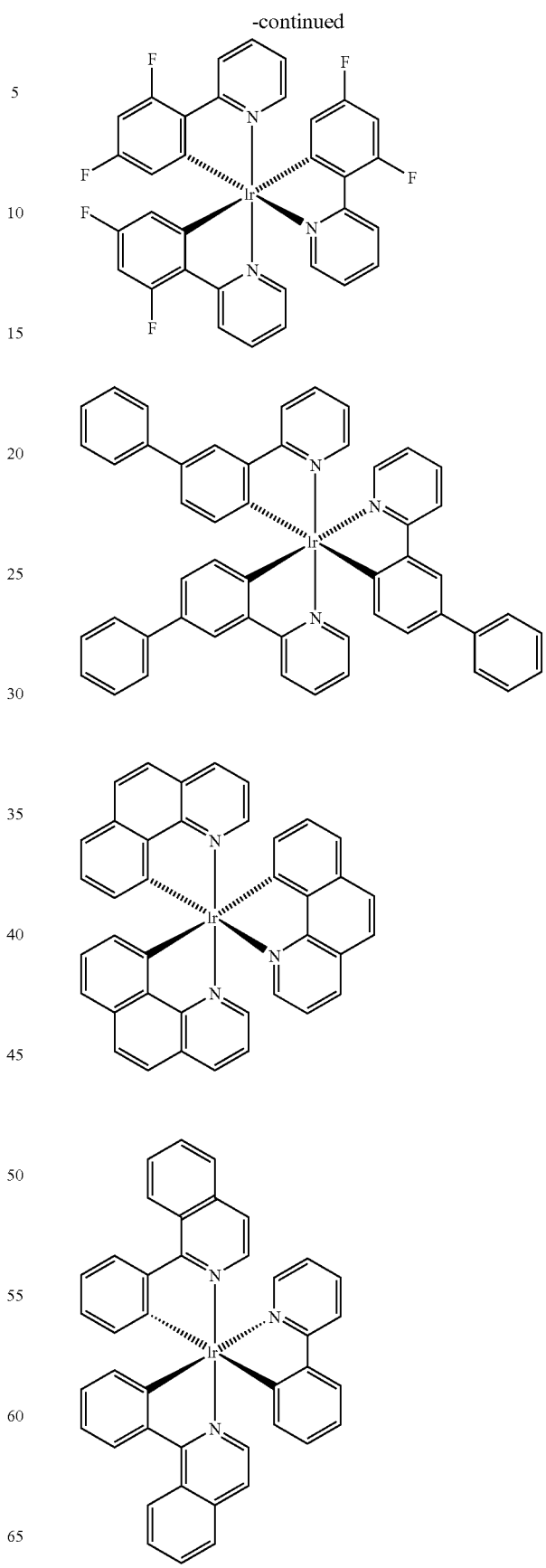

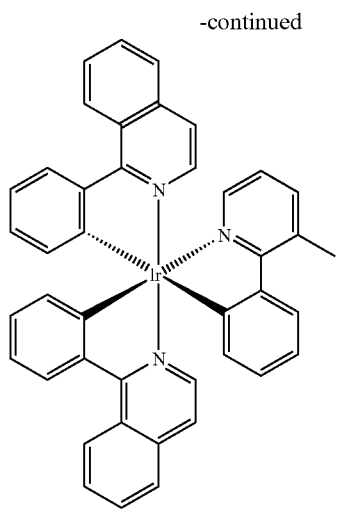
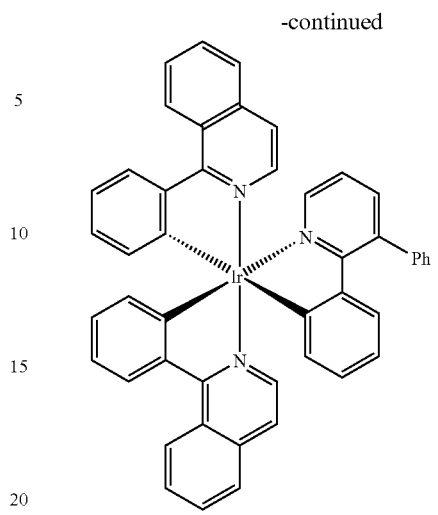
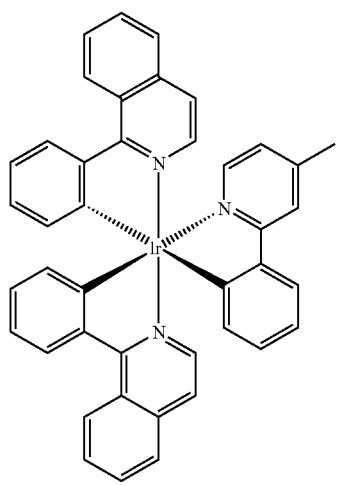
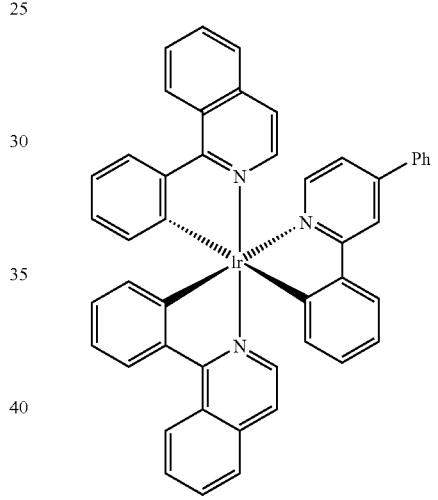
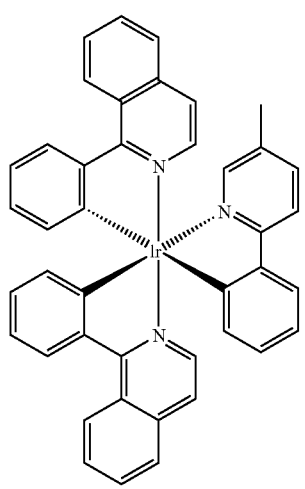
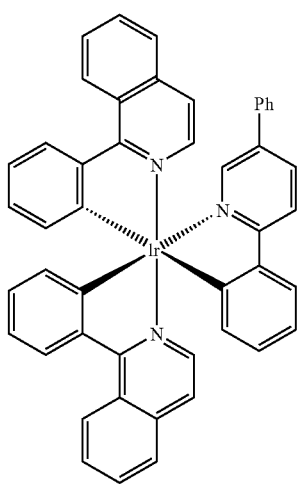

-continued

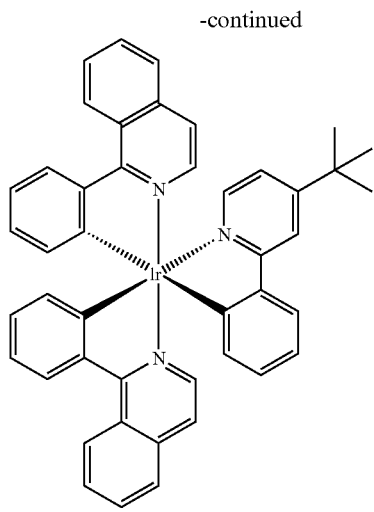

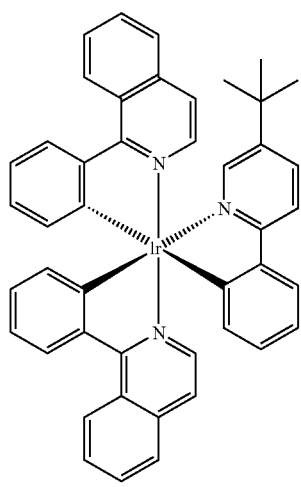

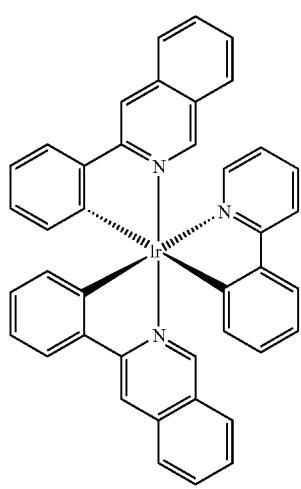

-continued

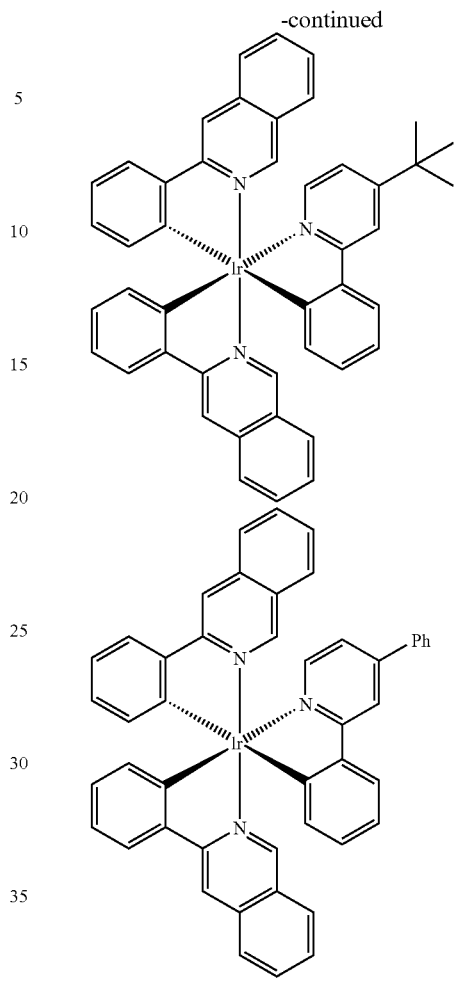

The isomerization reaction can be carried out by heating a solid composition containing meridional tris-cyclometallated Ir or Rh complex. Conveniently, a meridional isomer of tris-cyclometallated Ir or Rh compound represented by the formulas (1), (2), or (3) is heated at a temperature sufficient for isomerization to the corresponding facial isomer to take place. The starting material is in its solid state or crystalline state prior to heating, however, the starting material may melt or partially melt during isomerization depending upon the temperature employed in the process. The solid starting material may contain small amount of organic solvents that may form crystals with the metal complex or simply be trapped in the solid metal complex during isolation and/or purification, for example by precipitation or recrystallization from organic solvents. The ratio of the organic solvents contained in the starting solid material relative to the metal complex is usually not more than one molecule of organic solvents per molecule of the metal complex. In some cases, the ratio may be higher but generally not more than two molecules of the organic solvents per molecule of the metal complex.

Temperature employed in this process should be sufficient to overcome the energy barrier for the isomerization of meridional isomer to take place. Desirably, a higher temperature may be used to accelerate the isomerization process. Temperature required for the isomerization can vary depending on the structure of the starting meridional compounds. Usually, the temperature required for this transformation is greater than 150° C., suitably greater than 250° C., and desirably between 250-350° C. An optimal temperature can be attained by repeating experiments to ensure complete isomerization within reasonable period of time but to avoid any significant decomposition of the materials or formation of by products caused by high temperature.

The isomerization reaction can be carried out in either a sealed system or an open system under inert gas atmosphere. The isomerization can be carried out in a sealed system by placing the starting solid composition in a container then sealing the container under high vacuum. The container can be made of glass, metal, quartz, or other materials, conveniently the container is a glass ampoule. The container can be either directly placed in an oven or other heating apparatuses for the isomerization or placed in a secured device that can be heated to desired temperature by any means. Means of heating can include irradiation of microwaves.

The isomerization can be carried out in an open system or pressurized system. Desirably, such isomerization should be carried out under dry inert gas atmosphere. The inert gas can be nitrogen, helium, or argon. Conveniently the inert gas is nitrogen or argon, preferably argon.

Agitation may be required to achieve better heat conducting and uniformity of isomerization for larger scale process, reducing the time for complete isomerization and material decomposition due to long exposure to high temperature.

The formation of ligand-scrambling by-products in the isomerization of heteroleptic tris-cyclometallated iridium complexes is significantly suppressed. The reaction can be carried out at a temperature and for a period of time sufficient to form the facial isomer in >90% isomeric purity. Isomeric purity is defined as relative amount of the facial isomer to the total amount of both facial and meridional isomers. The product can be purified by column chromatography and/or recrystallization. Further, the purity of the desired compound can be further improved through sublimation.

Unless otherwise specifically stated, use of the term "group", "substituted" or "substituent" means any group or radical other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy)propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

SYNTHETIC EXAMPLES

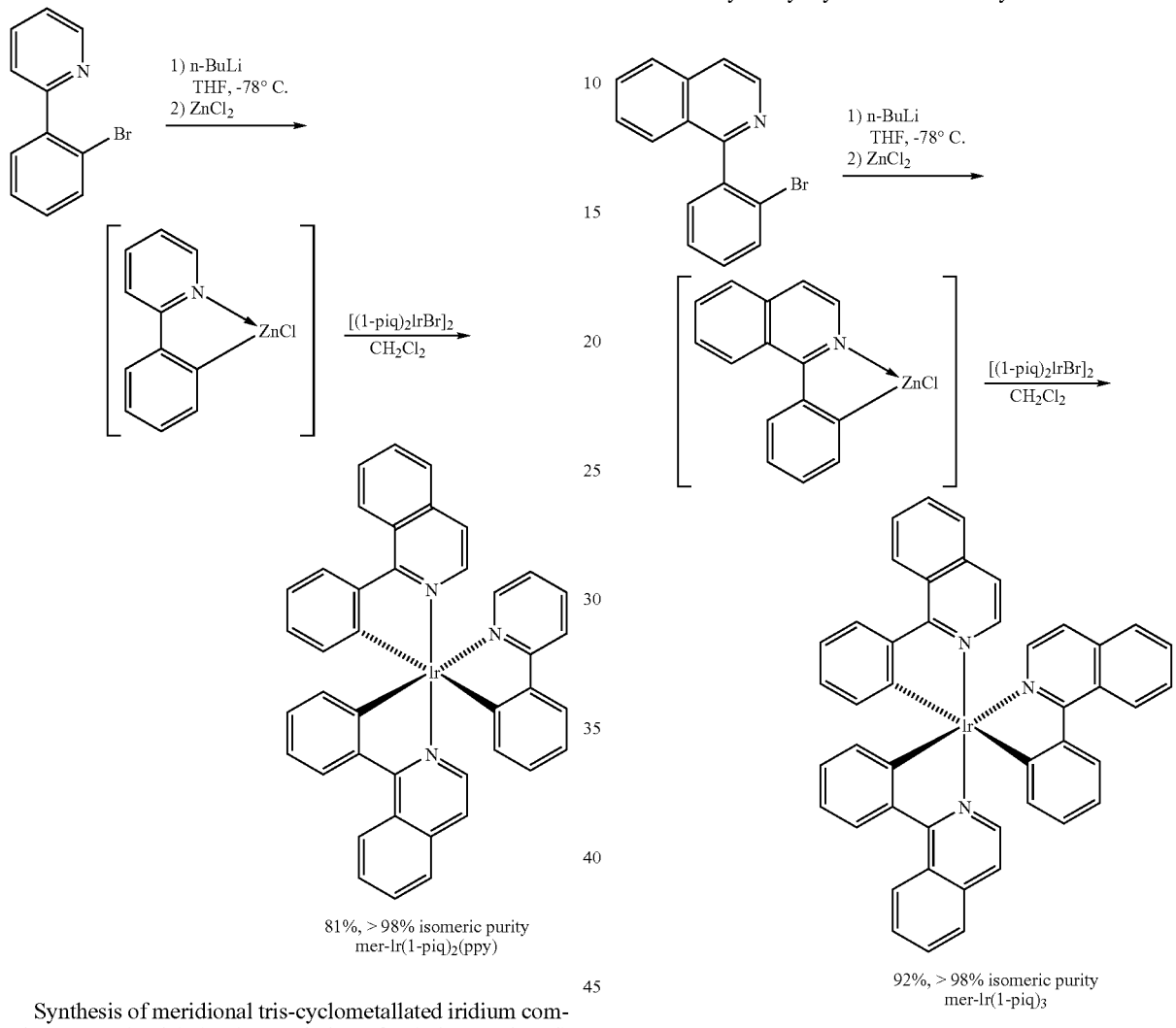

81%, >98% isomeric purity
mer-Ir(1-piq)₂(ppy)

Synthesis of meridional tris-cyclometallated iridium complex, mer-Ir(1-piq)₂(ppy): A solution of 1-(2-bromophenyl)pyridine (1.8 g, 7.5 mmol) in anhydrous THF (30 mL, Aldrich) was cooled to −78° C. with a dry ice-acetone bath. To this solution was added dropwise a solution of n-BuLi in hexanes (5.2 mL, 1.6 M, 8.3 mmol, Aldrich). The mixture was stirred at −78° C. for 30 min and a solution of ZnCl₂ in ether (7.5 mL, 1.0 M, 7.5 mmol, Aldrich) was added slowly via a syringe. The cooling bath was removed and the reaction mixture was warmed to about room temperature. The bromide-bridged dimer [Ir(piq)₂Br]₂ (2.03 g, 1.5 mmol) was added to the reaction mixture in one portion. Anhydrous dichloromethane (30 mL) was added. After the mixture was refluxed for 6 hours, any remaining organozinc reagent was quenched with 5 mL of methanol. The mixture was poured into water (200 mL) and extracted with dichloromethane (3×100 mL). The combined organic layers were washed with water (2×100 mL) and brine (200 mL) and dried over MgSO₄. After filtration, the solvents were evaporated and the crude materials were dissolved in minimum amount of hot dichloromethane. Addition of methanol led to the precipitation of the product, which was collected by filtration, washed thoroughly with methanol and diethyl ether, and dried in air to yield yellow orange solids, meridional bis-(1-(phenyl)isoquinoline-N,C²)(2-(phenyl)pyridinato-N,C²)iridium (III), 1.85 g, 82%. The product can be further purified by recrystallization. The meridional configuration of the titled compound has been confirmed by X-ray crystal structure analysis.

92%, >98% isomeric purity
mer-Ir(1-piq)₃

Preparation of mer-Ir(1-piq)₃. To a suspension of 1-(2-bromophenyl)isoquinoline (0.57 g, 2 mmol) in anhydrous ether (10 mL) cooled with a dry ice-acetone bath was added dropwise a solution of n-BuLi in hexanes (1.38 mL, 1.6 M, 2.2 mmol) via a syringe. After the reaction mixture was stirred at −78° C. for 30 min, a solution of ZnCl₂ in diethyl ether (2 mL, 1.0 M, 2 mmol) was added slowly via a syringe. The cooling bath was removed and the reaction mixture was warmed to room temperature. The bromide-bridged dimer [Ir(1-piq)₂Br]₂ (0.68 g, 0.5 mmol) was added to the reaction mixture in one portion. Anhydrous dichloromethane (20 mL) was added to accelerate the reaction. The mixture was refluxed for 24 h then cooling to room temperature. The red precipitates were collected by filtration and washed with dichloromethane, methanol and ether thoroughly, and dried in air, orange red solids, meridional tris-(1-(phenyl)isoquinoline-N,C²)iridium (III), yield: 92%. MS: m/z calcd 805.2; found 806.1 [M+1].

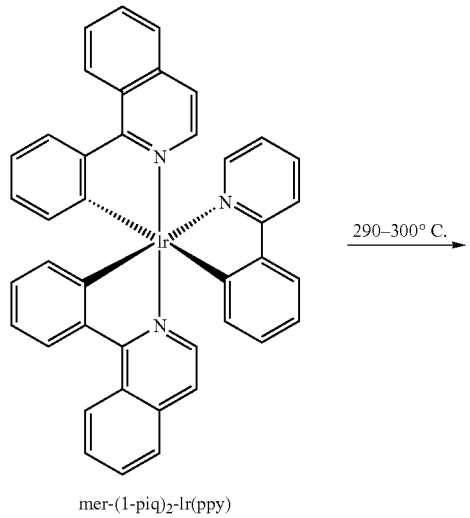

mer-(1-piq)$_2$-Ir(ppy)

$\xrightarrow{290-300° C.}$

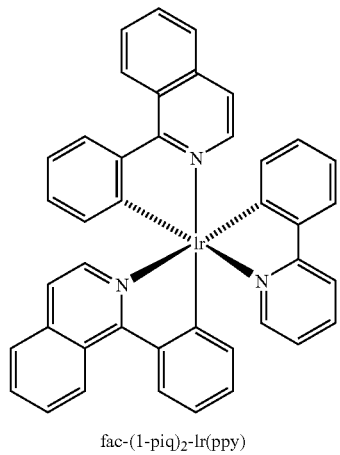

fac-(1-piq)$_2$-Ir(ppy)

Isomerization of meridional tris-cyclometallated iridium complex, mer-Ir(1-piq)$_2$(ppy): A sample of mer-Ir(1-piq)$_2$(ppy) (150 mg, mer/fac ratio >99:1, HPLC area) was placed in a opened small vial. The vial was placed into a heating apparatus with an inlet connected with a dry argon line and with an outlet connected to a bubbler. The heating apparatus was purged for 30 min before heating then maintained a slow argon flow during heating. The material was heated at 290° C. for 48 h. After cooling to room temperature, the vial was taken out and the mer/fac ratio of the sample was determined by HPLC to be 7:93 (HPLC area).

Isomerization of meridional tris-cyclometallated iridium complex mer-Ir(1-piq)$_3$: Using the same procedure described above, a sample of mer-Ir(1-piq)$_3$ (50 mg, mer/fac ratio >99:1, HPLC area) was heated at 300° C. under argon atmosphere for a period of 3 h to produce a material containing predominantly fac-Ir(1-piq)$_3$ (mer/fac ratio=17:83, HPLC area).

Isomerization of meridional tris-cyclometallated iridium complex mer-Ir(1-piq)$_2$(ppy) in sealed system: A sample of mer-Ir(1-piq)$_2$(ppy) (20 mg, mer/fac ratio >99:1) was placed in a small ampoule. The ampoule was sealed under high vacuum and placed in an oven. The temperature of the oven was set to 300° C. After 3 hour, the ampoule was taken out and cooling to room temperature, the mer/fac ratio of the sample was determined by HPLC to be 4:96 (area).

It should be mentioned that the reaction conditions described in the examples are not optimized and one skilled in the field can make some improvements by extensively optimizing the reaction parameters for each individual reaction.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

The invention claimed is:

1. A process for forming a facial tris-cyclometallated iridium or rhodium complex isomer comprising heating an original solid composition containing meridional isomer of the tris-cyclometallated iridium or rhodium metal complex at a temperature and for a time sufficient to form a product containing the facial tris-cyclometallated iridium or rhodium complex isomer in an increased ratio to meridional tris-cyclometallated iridium or rhodium complex isomer compared to the original composition.

2. The process of claim 1 wherein the tris-cyclometallated complex is a homoleptic complex of formula (1):

$$ML_3 \quad (1)$$

wherein:
M is the metal Ir or Rh; and
L is a monoanionic bidentate ligand that can be coordinated to M through a carbon and a heteroatom donor.

3. The process of claim 1 wherein the tris-cyclometallated complex is a heteroleptic complex of formula (2-):

$$M(L')_2L'' \quad (2)$$

or formula (3):

$$ML'L''L''' \quad (3)$$

wherein either formula (2) or (3):
M is the metal Ir or Rh; and
L', L'', and L''' are monoanionic bidentate ligands that can be coordinated to M through a carbon and a heteroatom donor.

4. The process of claim 3 wherein the heteroleptic tris-cyclometallated complex contains two different ligand groups.

5. The process of claim 4 wherein at least one of the ligands is a 1-phenylisoquinoline group or a 3-phenylisoquinoline group.

6. The process of claim 4 wherein at least one of the ligands is a 1-phenylisoquinoline represented by the formula:

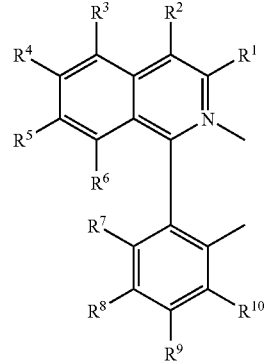

wherein $R^1$-$R^{10}$ each represent hydrogen or independently selected substituent groups.

7. The process of claim 4 wherein at least one of the ligands is a 3-phenylisoquinoline group represented by the formula:

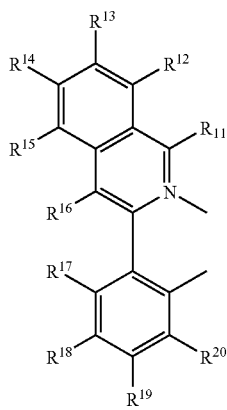

wherein $R^{11}$-$R^{20}$ each represent hydrogen or independently selected substituent groups.

8. The process of claim 4 wherein two of the ligands are 1-phenylisoquinoline groups and the other is a phenylpyridine group.

9. The process of claim 8 wherein the phenylpyridine ligand group is one selected from the substituted or unsubstituted forms of the following groups:

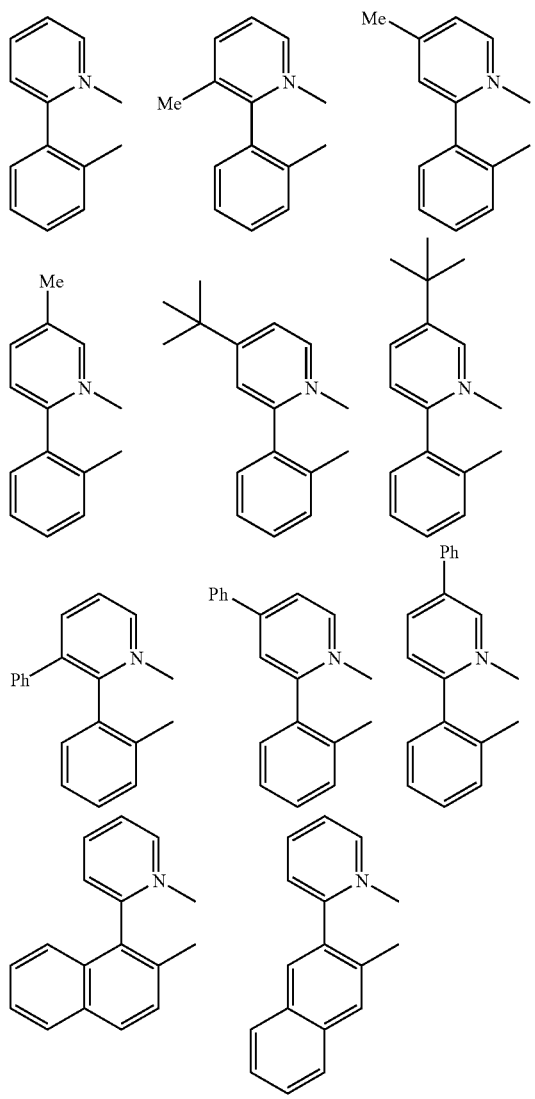

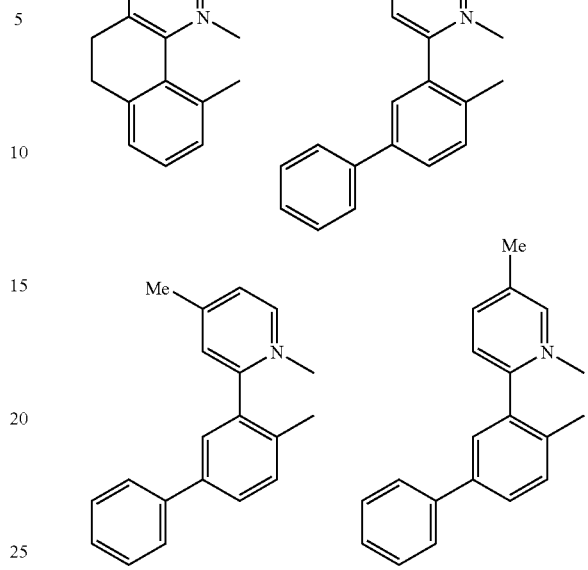

10. The process of claim 1 wherein the isomerization is performed in a sealed system.

11. The process of claim 1 wherein the isomerization is performed in an open system.

12. The process of claim 11 wherein the open system is under protection of dry inert gas atmosphere.

13. The process of claim 12 wherein the inert gas is nitrogen.

14. The process of claim 12 wherein the inert gas is argon.

15. The process of claim 1 wherein the solid composition contains organic solvent molecules.

16. The process of claim 15 wherein the amount of the organic solvent molecules in the original composition is not more than 2 molecules of the organic solvents per molecule of the complex.

17. The process of claim 15 wherein the amount of the organic solvent molecules in the original composition is not more than 1 molecule of the organic solvents per molecule of the complex.

18. The process of claim 1 wherein the isomerization reaction is carried out at a temperature greater than 150° C.

19. The process of claim 18 wherein the temperature is greater than 250° C.

20. The process of claim 18 wherein the temperature is between 250° C. and 350° C.

21. The process of claim 1 wherein agitation is provided during the reaction.

22. The process of claim 1 wherein the heating is conducted by irradiation of microwaves.

23. The process of claim 1 wherein the reaction is carried out at a temperature and for a period of time sufficient to form the facial isomer in >90% isomeric purity.

24. The process of claim 1 wherein the reaction product is further purified by sublimation or recrystallization.

* * * * *